United States Patent [19]

Baker et al.

[11] Patent Number: 4,845,107
[45] Date of Patent: Jul. 4, 1989

[54] FUNGICIDAL N-PYRIDYL HALOAMIDES

[75] Inventors: Don R. Baker, Orinda; Keith H. Brownell, San Jose, both of Calif.

[73] Assignee: ICI Americas Inc., Wilmington, Del.

[21] Appl. No.: 114,801

[22] Filed: Oct. 29, 1987

[51] Int. Cl.$^4$ ............ C07D 213/64; C07D 213/74; A01N 43/40

[52] U.S. Cl. .................... 514/346; 514/352; 546/292; 546/309

[58] Field of Search .............. 546/292, 309; 514/346, 514/352

[56] References Cited

U.S. PATENT DOCUMENTS 4,137,070 1/1979 Pallos et al. ............ 71/100

Primary Examiner—Alan L. Rotman
Attorney, Agent, or Firm—Michael J. Bradley

[57] ABSTRACT

Novel fungicidal pyridyl cyclopropane carboxamides having the general structural formula

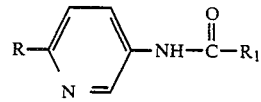

wherein R is selected from the group consisting of $C_1$–$C_3$ alkoxy, $C_1$–$C_3$ haloalkoxy and halogen; and $R_1$ is $C_1$–$C_6$ haloalkyl; and fungicidally acceptable organic and inorganic salts thereof.

11 Claims, No Drawings

FUNGICIDAL N-PYRIDYL HALOAMIDES

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infection, could control the fungi and eliminate the deleterious effects by use of a postinfection curative spray.

SUMMARY OF THE INVENTION

Novel fungicidal N-pyridyl haloamides having the formula $$R-\text{pyridyl}-NH-\overset{O}{\underset{\|}{C}}-R_1$$

wherein

R is selected from the group consisting of $C_1-C_3$ alkoxy such as propoxy, ethoxy and methoxy, preferably methoxy, $C_1-C_3$ haloalkoxy and halogen, preferably chlorine;

$R_1$ is $C_1-C_6$ haloalkyl, preferably halomethyl; and fungicidally acceptable organic and inorganic salts thereof which are highly effective fungicides for use both as preventive and curative fungicides are disclosed herein.

The term "fungicide" is used to mean a compound which controls fungal growth. "Controls" includes prevention, destruction and inhibition of fungal growth. The term "curative" is meant to refer to post-infection application of a fungicide which establishes control of fungal infection and prevents development of deleterious effects of the fungi on the host crop.

DETAILED DESCRIPTION

The novel fungicidal compounds of this invention are pyridyl cyclopropane carboxyamides having the general formula $$R-\text{pyridyl}-NH-\overset{O}{\underset{\|}{C}}-R_1$$

wherein

R is selected from the group consisting of $C_1-C_3$ alkoxy such as propoxy, ethoxy and methoxy, preferably methoxy, $C_1-C_3$ haloalkoxy and halogen, preferably chlorine;

$R_1$ is $C_1-C_6$ haloalkyl, preferably halomethyl; and fungicidally acceptable organic and inorganic salts thereof.

By the term "$C_1-C_3$ alkoxy" is meant methoxy, ethoxy, propoxy and isopropoxy.

By the term "$C_1-C_6$ haloalkyl" is meant one or more halogen atoms substituted on a $C_1-C_6$ alkyl radical.

By the term "$C_1-C_3$ haloalkoxy" is meant halogen substituted methoxy, ethoxy, propoxy and isopropoxy.

The compounds of this invention can be generally prepared by reacting a properly substituted aminopyridine with a properly substituted haloalkanoyl chloride or anhdydride in a non-polar solvent such as dichloromethane in a suitable reactor. It is desirable to maintain an acid scavenger such as pyridine in the reaction vessel. The reaction generally will proceed at room temperature but will operate at a temperature range from $-30°$ to $60°$ C., depending on the substitutions on the amino pyridine and the carboxylic acid chloride or anhydride. The reaction should go to completion within 1 to 3 hours. The acid salt may be recovered directly if no acid scavenger was used in the reaction or the free base product is recovered in a conventional manner by washing with an alkali solution such as sodium hydroxide and water, drying over conventional drying agents such as magnesium sulfate, and crystallizing from hexane.

Salts of the various haloalkanoylmides can be conventionally prepared by reacting at least a molar amount of a Lewis acid with the carboxamide. Preferably the reaction is run in a solvent for the carboxamide. The prepared salt is recovered from the reaction mixture by conventional techniques.

N-Pyridyl haloamides of the invention are basic. The uprotonated nitrogen atom of the pyridyl ring can be protonated by an acid, either organic or inorganic. Representation inorganic acids are hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also fungicidal.

EXAMPLE 1

Preparation of N-(2-Methoxy-5-pyridyl)-dichloroacetamide

Dichloroacetyl chloride, 97% (2.0 ml, 0.03 mol) was added over a period of 30 seconds to a mixture of 5-amino-2-methoxypyridine (3.7 g, 0.03 mol), pyridine (5.0 ml) and methylene chloride (100 ml). The reaction was exothermic and allowed to stand at room temperature for one hour. The reaction was then washed with 5% sodium carbonate solution (2×100 ml), dried over anhydrous magnesium carbonate, filtered, and evaporated in vacuo to give a solid that was triturated with hexane to yield 6.4 g of the title compound, m.p. 104°–107° C. The title product was identified by infrared (IR), nuclear magnetic resonance (NMR) and mass spectrocopy (MS) analysis.

EXAMPLE 2

Preparation of N-(2-Methoxy-5-pyridyl)-chloroacetamide hydrochloride

Chloroacetyl chloride (8.0 ml, 0.10 mol) was added over a period of 10 minutes with cooling (dry ice bath) to a solution of 5-amino-2-methoxypyridine (11 ml, 0.10 mol) and ether (100 ml). After one hour the reaction wsa filtered and the solid collected and washed with ether to give 10.7 g of the title compound, m.p. 155°–160° C. The title product was identified by IR, NMR and MS analysis.

EXAMPLE 3

Preparation of N-(2-Methoxy-5-pyridyl)-chloroacetamide

The filtrate from the preparation of the compound in Example 2 was washed with saturated sodium bicarbonate (200 ml) and hexane (50 ml) added. The solid was filtered off and dried to give 9.4 g of the title compound, mp. 74°-76° C. The title product was identified by IR, NMR and MS analysis.

EXAMPLE 4

Preparation of N-(2-Methoxy-5-pyridyl)-difluoroacetamide

Difluoracetic acid was added to a mixture of carbonyl diimidazole (8.4 g, 0.052 mol) and methylene chloride (100 ml) under a nitrogen atmosphere. Gas was evolved and a new solid formed in the reaction. After stirring at room temperature for 30 minutes, 5-amino-2-methoxypyridine (5.7 ml, 0.052 mol) was added over a two-minute period. The reacion was slightly exothermic and was stirred further for another 30 minutes when it was washed with water (100 ml), 5% aqueous acetic acid (2×50 ml), 5% sodium bicarbonate (25 ml); dried over anhydrous magnesium sulfate; filtered; and evaporated in vacuo to give an oil. The oil was extracted with ether and the ether extract on dilution with pentane gave 3.7 g of crude product. This was extracted with ether and diluted with pentane to give 2.0 g of the title compound, m.p. 75°-78° C. The title product was identified by IR, NMR and MS analysis.

Representative cmpounds of this invention and their physical properties are shown in Table I.

TABLE I

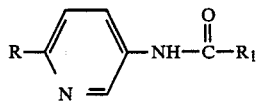

| Cmpd. No. | R | $R_1$ | melting point °C. |
|---|---|---|---|
| 1 | —OCH$_3$ | —CHCl$_2$ | 104.0–107.0° C. |
| 2 | —OCH$_3$ | —CF$_3$ | 66.0–70.0° C. |
| 3 | the trifluoroacetic acid salt of Cmpd. 2 | | 90.0–92.0° C. |
| 4 | —OCH$_3$ | —CH$_2$Cl | 74.0–76.0° C. |
| 5 | the hydrochloric acid salt of Cmpd. 4 | | 155.0–160.0° C. |
| 6 | —OCH$_3$ | —CF$_2$Cl | 74.0–78.0° C |
| 7 | the difluorochloroacetic acid salt of Cmpd. 6 | | 89.0–90.0° C. |
| 8 | —OCH$_3$ | —CF$_2$H | 105.0–120.0° C. |
| 9 | —OCH$_3$ | —CCl$_3$ | 77.0–81.0° C. |
| 10 | —OCH$_3$ | —C$_2$F$_5$ | 100.0–102.0° C. |
| 11 | the pentafluoroacetic acid salt of Cmpd. 10 | | 106.0–107.0° C. |
| 12 | —Cl | —CF$_3$ | 110.0–111.0° C. |
| 13 | —Cl | —CF$_2$Cl | 95.0–97.0° C. |

EXAMPLE 5

Preventative Spary Evaluation Procedures

Barley Powdery Mildew (PM)

Northrup King Sunbar 401 barley seed is planted (12 seeds/2" pot) in a sandy-loam soil seven days prior to testing. The test compound is diluted in a 50/50 acetone/water solution to produce concentrations decreasing from 2250 µg/ml. The test solution is then sprayed onto the barley plants with atomizing sprayers.

Twenty-four hours later, test plants are plced in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation greenhouse bench.

Results are recorded seven days following inoculation as percent disease control based on the persent reduction in infected area as compared to the untreated control plants. Compound concentrations which provide 90% disease control (EC 90) are determined from dosage/dilution curves.

Leaf Rust (LR)

Seven seeds of Anza wheat are planted in 2" pots in a sandy-loam soil 12 days prior to testing. The compound to be tested is diluted with a 50/50 acetone/water solution to produce concentrations decreasing from 2250 µg/ml. Twelve ml of test solution are sprayed onto the wheat plants with an atomizing sprayer.

A suspension of *Puccinia recondita* urediospores is prepared by vacuuming spores from wheat leaves with ureida pustules and suspending 10$^5$ spores/ml in deionized water plus 0.5% Tween ® 20 (polyoxyethylene sorbitan monolaurate). Plants are inoculated 24 hours after treatment by spraying with the spore suspension to runoff, allowing it to dry on the leaves, respraying to runoff, and then placing the plants into a mist chamber. Following 48 hours in the mist, plants are moved to a subirrigation greenouse bench.

Results are recorded ten days following inoculation as percent disease control based on the percent reduction in lesion area as compared to the untreated control plants. Compound concentrations which provide 90% disease control (EC 90) are determined from dosage/dilution curves.

Botrytis Blight (BB)

Two white rose petals are place din a petri dish lined with wet filter paper. The compound to be tested is diluted with a 50/50 acetone/ water solution to produce concentrations decreasing from 2250 µg/ml. Onehalf ml of test solution is atomized onto the petals, and allowed to dry.

Inoculum is prepared by adding a 5 mm plug from a two-week old *Botrytis cinerea* culture grown on Elliot's V-8 agar, to 10 ml sterile distilled water plus 0.5 ml grape juice. A 20 µl drop of this inoculum suspension is placed on each petal. Petri dishes with inoculated petals are stored in sealed plastic boxes to maintain saturated humidity.

Results are read four days following inoculation as a precent reduction in necrotic area compared to the acetone/water controls. Compound concentrations which provide 90% disease control (EC 90) are determined from dosage/dilution curves.

The results are presented in Table II as an approximate EC 90 in parts per million. 2250 ppm equals 2250 µg/ml. The entry (750) indicates partial control at 750 ppm. the entry "*" indicates no control at 750 ppm. The entry (2250) indicates partial control at 2250 ppm. Only selected compounds were tested at 2250 ppm.

TABLE II

| Cmpd. No. | LR | BB |
|---|---|---|
| 1 | (750) | (750) |
| 2 | * | 150 |
| 3 | * | 60 |
| 4 | * | 250 |
| 5 | (750) | 60 |

TABLE II-continued

| Cmpd. No. | LR | BB |
|---|---|---|
| 6 | * | 50 |
| 7 | * | 80 |
| 8 | * | (750) |
| 9 | * | (750) |
| 10 | (2250) | 2250 |
| 11 | 2250 | (2250) |
| 12 | (2250) | (2250) |
| 13 | (2250) | * |

The compounds of this invention are particularly effective against Botrytis Bud Blight and are particularly effective as preventative foliar sprays and curative foliar sprays when compared to standard commercial compounds used as Botrytis preventative and curative sprays. Fungi on which the compounds of the present invention are particularly effecitve are *Botrytis cinerea* and *Puccinia graminis*.

The compounds of the present invention are sueful as fungicides, especially as preventative or curative fungicides, and can be applied in a variety of ways at various concentrations. In general, these compounds and formulations of these compounds can be applied directly to the crop foliage, the soil in which the crop is growing, or in the irrigation water for the crop or soil. In practice, the compounds herein defined are formulated into fungicidal compositions, by admixutre, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifialbe concentrates, as powdery dusts, as solutions or as any of several other known types of formulations, depending upon the desired mode of application. Preferred formulations for preventative or curative fungicidal applications are wettable powders and emulsifiable concentrates. These formulations may contain as little as about 0.1% to as much as about 95% or more by weight of active ingredient. A fungicidally effective amount depends upn the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil or plant either as a dry dust or as a dispersion in water or other liquid. Typical carriers for wettable powders include Fuller's earth, kaoline clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil or plant as a dispersion in water or other liquid. These granules are dust-free and free flowing when dry and yet upon dilution in water, form homogeneous dispersions. Typical carriers for dry flowables include fuller's earth, kaolin clays, silica and other readily wet organic or inorganic diluents. The dry flowables normally are prepared to contain from about 5% to about 95% of the active ingreident and usually contain a small amount of wetting, dispersing or emulsifying agent to facilitate wetting and dispersion.

Emulsifiable concentrates are homogenous liquid compositions which are dispensible in water or other dispersant, and may consist entirely of the active compound with a liquid or solid emulsifying agent, or may also contain a liquid carrier, such as xylene, heavy aromatic naphtha, isophorone and other non-volatile organic solvents. for fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formulations include, for example, the alkyl and alkylaryl sulfonates and sulfates and their sodium salts; polyhydroxy alcohls; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
|---|---|---|---|
| Ingredient | | | Weight % |
| Oil | | | |
| Compound 1 | | | 1 |
| Oil solvent-heavy aromatic naphtha | | | 99 |
| Total | | | 100 |
| Emulsifiable Concentrate | | | |
| Compound 2 | | | 50 |
| Kerosene | | | 45 |
| Emulsifying agent (mixture of long chain ethoxylated polyethers with long chain sulfonate) | | | 5 |
| Total | | | 100 |
| Emulsifiable Concentrate | | | |
| Compound 3 | | | 90 |
| Kerosene | | | 5 |
| Emulsifying agent (mixture of long chain ethoxylated polyethers with long chain sulfonate) | | | 5 |
| Total | | | 100 |
| Ingredient | Wt. % | Wt. % | Wt. % |
| Dusts and/or Powders | | | |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingreident in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the sut and liquid compositions can be applied to the plant by the use of power-dusters, boom and hand sprayers and spray dusters. The compositions can also be applied from airplanes as a dust or a spray because they are effective in low dosages.

We claim:

1. A compound having the structural formula

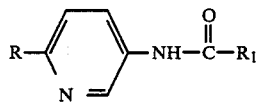

wherein R is selected from the group consisting of $C_1$–$C_3$ alkoxy, $C_1$–$C_3$ haloalkoxy and halogen; and $R_1$ is $C_1$–$C_6$ haloalkyl; or a fungicidally acceptable organic or inorganic salt thereof.

2. The trifluoroacetic acid salt of the compound of claim 1 wherein R is —$OCH_3$ and $R_1$ is —$CF_3$.

3. The hydrochloric acid salt of the compound of claim 1 wherein R is —$OCH_3$ and $R_1$ is —$CH_2Cl$.

4. The compound of claim 1 wherein R is —$OCH_3$ and $R_1$ is —$CF_2Cl$.

5. The difluorochloroacetic acid salt of the compound of claim 1 wherein R is —$OCH_3$ and R is —$CF_2Cl$.

6. The fungicidal composition comprising a fungicidally effective amount of a compound having the structural formula

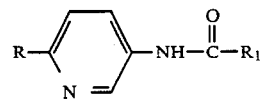

wherein R is selected from the group consisting of $C_1$–$C_3$ alkoxy, $C_1$–$C_3$ haloalkoxy and halogen; and $R_1$ is $C_1$–$C_6$ haloalkyl; or a fungicidally acceptable organic or inorganic salt thereof in combination with an adjuvant or carrier.

7. The method of controlling fungi comprising applying to the area where control is desired, a fungicidally effective amount of a compound having the formula

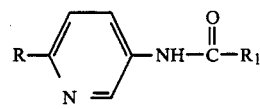

wherein R is selected from the group consisting of $C_1$–$C_3$ alkoxy, $C_1$–$C_3$ haloalkoxy and halogen; and $R_1$ is $C_1$–$C_6$ haloalkyl; or a fungicidally acceptable organic or inorganic salt thereof.

8. The method of claim 7 wherein the compound is the trifluoroacetic acid salt of the compound of claim 2 wherein R is —$OCH_3$ and $R_1$ is —$CF_3$.

9. The method of claim 7 wherein the compound is the hydrochloric acid salt of the compound of claim 1 wherein R is —$OCH_3$ and $R_1$ is —$CH_2Cl$.

10. The method of claim 7 wherein the compound is the difluorochloracetic acid salt of the compound wherein R is —$OCH_3$ and $R_1$ is —$CF_2Cl$.

11. The method of claim 7 wherien R is —$OCH_3$ and $R_1$ is —$CH_2Cl$.

* * * * *